US007276643B2

(12) United States Patent
Masliah et al.

(10) Patent No.: US 7,276,643 B2
(45) Date of Patent: *Oct. 2, 2007

(54) TRANSGENIC ANIMALS, CELL LINES DERIVED THEREFROM, AND METHODS FOR SCREENING FOR ANTI-AMYLOIDOGENIC AGENTS

(75) Inventors: Eliezer Masliah, San Diego, CA (US); Edward Rockenstein, Chula Vista, CA (US); Margaret Mallory, deceased, late of Encinitas, CA (US); by Hersey Mallory, legal representative, Encinitas, CA (US)

(73) Assignee: The Regents of the University of California, Oakland, CA (US)

( * ) Notice: Subject to any disclaimer, the term of this patent is extended or adjusted under 35 U.S.C. 154(b) by 416 days.

This patent is subject to a terminal disclaimer.

(21) Appl. No.: 10/204,337

(22) PCT Filed: Feb. 20, 2001

(86) PCT No.: PCT/US01/05569

§ 371 (c)(1), (2), (4) Date: May 22, 2003

(87) PCT Pub. No.: WO01/60794

PCT Pub. Date: Aug. 23, 2001

(65) Prior Publication Data

US 2004/0128706 A1 Jul. 1, 2004

Related U.S. Application Data

(60) Provisional application No. 60/183,571, filed on Feb. 18, 2000.

(51) Int. Cl.
A01K 67/027 (2006.01)
G01N 33/00 (2006.01)
C12N 5/02 (2006.01)

(52) U.S. Cl. .............................. 800/18; 800/3; 435/325
(58) Field of Classification Search .................. 800/18, 800/3; 435/325
See application file for complete search history.

(56) References Cited

OTHER PUBLICATIONS

Kahle PJ, Physiology and pathophysiology of alpha-synuclein cell culture and transgenic animal models based on a parkinson's disease-associated protein, 2000, Annals of the New York Academy of Sciences, vol. 920, pp. 33-41.*
Schneider MR, Transgenic mouse models for studying the functions of insulin-like growth factor-binding proteins, FASEB, 2000, vol. 14, pp. 629-640.*
Gotz J, In vivo analysis of wild-type and FTPD-17 tau transgenic mice, Annal of NY Acad of Sci, 2000, vol. 920, pp. 126-133.*
Ristevski S, Making better transgenic models, 2005, Molecular Biotechnology, vol. 29, pp. 153-163.□□*
Houdebine LM, The methods to generate transgenic animals and to control transgene expression, 2002, J. of Biotechnology, vol. 98, pp. 145-160.*
Smith KR, Gene transfer in higher animals: theoretical considerations and key concepts, J. of Biotechnology, vol. 99, pp. 1-22.*
Cole, G.M. et al. Amyloid-Associated α-Synuclein (NACP) Pathology in Aged Amyloid Precursor Transgenic Mice. Society for Neuroscience Abstracts, 1999, vol. 25, No. 1-2, pp. 298, lines 7-19.
Davis, Stephen W. et al. Formation of Neuronal Intranuclear Inclusions Underlies the Neurological Dysfunction in Mice Transgenic for the HD Mutation. Cell, 1997, vol. 90, 537-548.
Games, Dora et al. Alzheimer-type neuropathology in transgenic mice overexpressing V717F β-amyloid precursor protein. Nature, 1995, vol. 373, 523-527.
Goldberg, M.S. et al. Studies of Human α-Synuclein in Transgenic Mice. Society for Neuroscience Abstracts, 1999, vol. 25, No. 1-2, lines 6-20.
Hashimoto, Makoto et al. Human recombinant NACP/α-synuclein is aggregated and fibrillated in vitro: Revelance for Lewy body disease. Brain Research, 1998, vol. 799, No. 2, 301-306.
Jensen, Paul H. et al. Binding of Aβ to α- and β-synucleins: identification of segments in α-synuclein/NAC precursor that bind Aβ and NAC. Biochem J. 1997, vol. 323, 539-546.
Mucke, L. et al. Potential Roles of α1-Antichymotrypsin and α-Synuclein in Alzheimer's Pathogenesis Assessed in Bigenic Mice Expressing Human Amyloid Precursor Proteins. Society for Neuroscience Abstracts, 1999, vol. 25, No. 1-2, p. 302, lines 4-21.
Mucke, Lennart et al. Protection Against HIV-1 gp120-induced Brain Damage by Neuronal Expression of Human Amyloid Precursor Protein. J.Exp.Med., 1995, vol. 181, 1551-1556.
Takeda, Ayako et al. Abnormal Accumulation of NACP/α-Synuclein in Neurodegenerative Disorders, Am. J. of Pathology, 1998, vol. 152, No. 2, 367-372.

* cited by examiner

Primary Examiner—Sumesh Kaushal
Assistant Examiner—David A. Montanari
(74) Attorney, Agent, or Firm—Morrison & Foerster LLP

(57) ABSTRACT

The methodologies of the present invention demonstrate that a critical balance between pro- and anti-amyloidogenic molecules exists that regulates amyloid formation and cell death in Alzheimer's disease and Parkinson's disease. β-Synuclein, the non-amyloidogenic homologue of α-synuclein, is a negative modulator of α-synuclein and Aβ aggregation, having neuroprotective properties against α-synuclein and Aβ neurotoxicity and that β-synuclein and therapeutic agents derived therefrom block amyloidogenesis and neurodegeneration in vivo. The method of the present invention establishes that β-synuclein blocks Aβ aggregation either by direct inhibition of Aβ amyloidogenesis or indirectly via either α-synuclein or its 35 a.a. NAC region, inferring neuroprotective characteristics within the effected cells. The generation of a transgenic mouse line and a cell system overexpressing α-synuclein characterizes the mechanisms by which β-synuclein blocks α-synuclein and Aβ aggregation and that this mechanism offers protection to the cell against amyloid formation as seen in the pathologies of Alzheimer's disease and Parkinson's disease.

7 Claims, 12 Drawing Sheets

SEQUENCE LISTING

```
<160> NUMBER OF SEQ ID NOS: 15

<210> SEQ ID NO 1
<211> LENGTH: 37
<212> TYPE: PRT
<213> ORGANISM: Artificial sequence
<220> FEATURE:
<223> OTHER INFORMATION: fusion of two mouse proteins
<220> FEATURE:
<221> NAME/KEY: MISC_FEATURE
<222> LOCATION: (1)..(37)
<223> OTHER INFORMATION: Beta-synuclein sequence inserted into NAC

<400> SEQUENCE: 1

Lys Glu Gln Ala Ser His Leu Gly Gly Ala Val Phe Ser Gly Val Thr
1               5                   10                  15

Ala Val Ala Gln Lys Thr Val Glu Gly Ala Gly Asn Ile Ala Ala Ala
            20                  25                  30

Thr Gly Leu Val Lys
```

<210> SEQ ID NO 2
<211> LENGTH: 37
<212> TYPE: PRT
<213> ORGANISM: Artificial Sequence
<220> FEATURE:
<223> OTHER INFORMATION: fusion of two mouse proteins
<220> FEATURE:
<221> NAME/KEY: MISC_FEATURE
<222> LOCATION: (1)..(37)
<223> OTHER INFORMATION: Beta-synuclein sequence inserted into NAC

<400> SEQUENCE: 2

Lys Glu Gln Val Thr Asn Val Gly Gly Ala Val Val Thr Gly Val Thr
1               5                   10                  15

Ala Val Ala Gln Lys Thr Val Glu Gly Ala Gly Asn Ile Ala Ala Ala
            20                  25                  30

Thr Gly Leu Val Lys
        35

<210> SEQ ID NO 3
<211> LENGTH: 423
<212> TYPE: DNA
<213> ORGANISM: Homo sapiens

<400> SEQUENCE: 3
atggatgtat tcatgaaagg actttcaaag gccaaggagg gagttgtggc tgctgctgag    60
aaaaccaaac agggtgtggc agaagcagca ggaaagacaa agagggtgt tctctatgta   120 ggctccaaaa ccaaggaggg agtggtgcat ggtgtggcaa cagtggctga aagaccaaa   180 gagcaagtga caaatgttgg aggagcagtg gtgacgggtg tgacagcagt agcccagaag   240
acagtggagg gagcagggag cattgcagca gccactggct ttgtcaaaaa ggaccagttg   300
ggcaagaatg aagaaggagc cccacaggaa ggaattctgg aagatatgcc tgtggatcct   360
gacaatgagg cttatgaaat gccttctgag gaagggtatc aagactacga acctgaagcc   420
taa                                                                423

<210> SEQ ID NO 4
<211> LENGTH: 249
<212> TYPE: DNA
<213> ORGANISM: Homo sapiens

<400> SEQUENCE: 4
ccgccgctcc atccccagcc ccggccccgc atccaggccg ccaggatgga cgtgttcatg    60
aagggcctgt ccatggccaa ggagggcgtt gtggcagccg cggagaaaac caagcagggg   120
gtcaccgagg cggcggagaa gaccaaggag ggcgtcctct acgtcggaag caagacccga   180
gaaggtgtgg tacaaggtgt ggcttcagtg gctgaaaaaa ccaaggaaca ggcctcacat   240
ctgggagga                                                          249

<210> SEQ ID NO 5
<211> LENGTH: 210
<212> TYPE: DNA
<213> ORGANISM: Homo sapiens

<400> SEQUENCE: 5
atggatgtct tcaagaaggg cttctccatc gccaaggagg gcgtggtggg tgcggtggaa    60
aagaccaagc aggggtgac ggaagcagct gagaagacca ggagggggt catgtatgtg   120

```
ggagccaaga ccaaggagaa tgttgtacag agcgtgacct cagtggccga gaagaccaag    180
gagcaggcca acgcggtgag cgaggctgtg                                     210
```

<210> SEQ ID NO 6
<211> LENGTH: 80
<212> TYPE: DNA
<213> ORGANISM: Homo sapiens

<400> SEQUENCE: 6

```
tgggatgttt gagacttctc tcctcaatgg tgacagttgg tcaccctgtt ctgcttcagg    60
gtttcagtac tgctcagtgt                                                80
```

<210> SEQ ID NO 7
<211> LENGTH: 15
<212> TYPE: PRT
<213> ORGANISM: Homo sapiens

<400> SEQUENCE: 7

```
Met Asp Val Phe Met Lys Gly Leu Ser Met Ala Lys Glu Gly Val
1               5                   10                  15
```

<210> SEQ ID NO 8
<211> LENGTH: 13
<212> TYPE: PRT
<213> ORGANISM: Homo sapiens

<400> SEQUENCE: 8

```
Val Val Ala Ala Ala Glu Lys Thr Lys Asn Gly Val Thr
1               5                   10
```

<210> SEQ ID NO 9
<211> LENGTH: 11
<212> TYPE: PRT
<213> ORGANISM: Homo sapiens

<400> SEQUENCE: 9

```
Glu Ala Ala Glu Lys Thr Lys Glu Gly Val Leu
1               5                   10
```

<210> SEQ ID NO 10
<211> LENGTH: 12
<212> TYPE: PRT
<213> ORGANISM: Homo sapiens

<400> SEQUENCE: 10

```
Tyr Val Gly Ser Lys Thr Arg Glu Gly Val Val Gln
1               5                   10
```

<210> SEQ ID NO 11
<211> LENGTH: 11
<212> TYPE: PRT
<213> ORGANISM: Homo sapiens

<400> SEQUENCE: 11

```
Gly Val Ala Ser Val Ala Glu Lys Thr Lys Glu
1               5                   10
```

<210> SEQ ID NO 12
<211> LENGTH: 20
<212> TYPE: DNA
<213> ORGANISM: Homo sapiens

<400> SEQUENCE: 12

```
gtggtgcatg gtgtggcaac                                                      20

<210> SEQ ID NO 13
<211> LENGTH: 21
<212> TYPE: DNA
<213> ORGANISM: simian virus 40

<400> SEQUENCE: 13
cagctggttc tttccgcctc a                                                    21

<210> SEQ ID NO 14
<211> LENGTH: 35
<212> TYPE: DNA
<213> ORGANISM: Homo sapiens

<400> SEQUENCE: 14
ccggtcgacc gccaccatgg acgtgttcat gaagg                                     35

<210> SEQ ID NO 15
<211> LENGTH: 31
<212> TYPE: DNA
<213> ORGANISM: Homo sapiens

<400> SEQUENCE: 15
ccgctcgagc ctacgcctct gctcatactc c                                         31
```

TRANSGENIC ANIMALS, CELL LINES DERIVED THEREFROM, AND METHODS FOR SCREENING FOR ANTI-AMYLOIDOGENIC AGENTS

This application is a national phase filing under 35 U.S.C. §371 and claims benefit of priority to Patent Convention Treaty (PCT) International Application Serial No. PCT/US01/05569, filed Feb. 20, 2001, which claims the benefit of priority of U.S. Provisional Application Ser. No. 60/183,571 to Eliezer Masliah et al., filed Feb. 18, 2000 and entitled "METHOD FOR SCREENiNG FOR ANTI-AMYLOIDOGENIC PROPERTTES AND METHOD FOR TREATMENT OF NEURODEGENERATIVE DISEASE", the entire contents of which are incorporated herein by reference.

FIELD OF THE INVENTION

This invention relates generally to methods for screening for and treatment of neurodegenerative diseases and more specifically to methods of measuring aggregation in neurons of α-, β-, and γ-synucleins and treatments utilizing synuclein and peptides derived therefrom as anti-amyloidogenic agents in vivo.

BACKGROUND

Parkinson's disease (PD), Alzheimer's disease (AD) and Lewy Body disease (LBD) are the most commonly found neurodegenerative disorders in the elderly population. Although their incidence continues to increase thus creating a serious public health problem, to date these disorders are neither curable nor preventable. Previous studies have shown that cognitive alterations seen with these disorders are most often associated with synaptic damage and that injury to the synapse might be associated with altered function of synaptic proteins. Among them, recent studies have pointed to α-synuclein, also known as the precursor of the non-Aβ component of Alzheimer's disease amyloid (NACP) as a major player in the pathogenesis of these diseases.

The neurodegenerative process in Parkinson's disease and Alzheimer's disease is characterized by extensive loss of selected neuronal populations accompanied by synaptic injury, astrogliosis and pathological hallmarks such as amyloid plaques, neurofibrillary tangles and neutrophil thread formation in Alzheimer's disease and the intraneuronal inclusions called Lewy bodies in Parkinson's disease. Parkinson's disease belongs to a heterogenous group of disorders presenting with parkinsonism and Lewy Body formation and which has been denominated Lewy body disease. Although the mechanisms triggering cell death and synaptic damage are unclear, the prevailing view is that neurodegeneration might result from gain of a toxic property of specific neuronal cell proteins, such as α-synuclein (in Parkinson's disease) and amyloid precursor protein (APP) (in Alzheimer's disease). In this regard, APP has been proposed to be centrally involved in Alzheimer's disease pathogenesis because mutations within this molecule are associated with familial forms of Alzheimer's disease, proteolytic products of APP processing abnormally accumulating in brains of Alzheimer's disease patients and overexpression of a mutant form of APP in transgenic mice mimics several aspects of Alzheimer's disease.

α-Synuclein, which belongs to a larger family of molecules including β- and γ-synuclein, is a 140 amino acid synaptic protein which is a precursor of the 35 amino acid amyloidogenic molecule non-amyloid component (NAC). α-Synuclein has been implicated in Parkinson's disease because it is abundantly found in Lewy Bodies, its overexpression in transgenic mice leads to Parkinson's disease-like pathology, and mutations within this molecule are associated with familial Parkinson's disease. While the precise mechanism by which α-synuclein and APP might interact during events leading to neurodegeneration are unclear, several studies support the contention that α-synuclein is involved in Alzheimer's disease because it abnormally accumulates in synapses and dystrophic neurites surrounding the plaques in Alzheimer's disease brain and NAG is present in amyloid plaque cores and promotes Aβ aggregation. Moreover, other studies have shown that both α-synuclein and Aβ aggregate under similar experimental conditions, and in familial Alzheimer's disease and Down's syndrome there is formation of α-synuclein-immunoreactive Lewy Bodies. Furthermore, a combined form of Parkinson's disease and Alzheimer's disease has also been associated with the widespread formation of α-synuclein-immunoreactive Lewy Bodies. Taken together, these studies support the possibility that interactions between α-synuclein and APP might lead to enhanced amyloidogenesis and neurodegeneration in disorders such as Parkinson's disease and Alzheimer's disease.

Several studies have suggested that neurons may be able to develop protective strategies against the neurotoxic effects of amyloid. For example, in neurodegenerative disorders associated with trinucleotide repeats, such as Frederick's ataxia, Myotonic dystrophy and Huntington's disease, formation of intraneuronal inclusion bodies might be protective, because the toxic proto-fibrils are sequestered. Similarly, in Parkinson's disease and Alzheimer's disease, is has been suggested that proto-rather than mature fibrils are neurotoxic. In this context, it is possible that the balance between amyloidogenic and anti-amyloidogenic molecules regulates neuronal survival. It is hypothesized that β-synuclein, the non-amyloidogenic homologue of α-synuclein, which naturally lacks the NAC domain, may inhibit amyloidogenesis and neurodegeneration. β-Synuclein is similar to α-synuclein in that it is abundantly expressed in the central nervous system, whereas γ-synuclein is expressed mainly in the peripheral nervous system. The relationship between α-synuclein and β-synuclein is strikingly similar to that of APP and its related protein APLP2 in that APLP2 is highly homologous with APP except for its Aβ domain and that it is non-amyloidogenic.

Human α-synuclein belongs to a larger family of synuclein proteins encoded by a gene on chromosome 4 and is highly abundant in the presynaptic terminals throughout the central nervous system (CNS). While the precise function of the synuclein superfamily of peptides is still unknown, several lines of evidence suggest potential roles in synaptic function and neural plasticity. Synelfin is the avian homologue to α-synuclein and PNP14 is the bovine homologue to human and murine β-synuclein, a phosphoprotein encoded by a gene on chromosome 5. More recently, γ-synuclein was isolated as a D3 synuclein-like molecule which was expressed predominantly in peripheral sympathetic neurons. γ-Synuclein was later cloned from the EST library as the breast cancer specific gene (BCSG1) whose expression was observed in invasive types of breast cancer. Human α-synuclein was originally isolated from plaques of Alzheimer's disease brains as a 19-kD protein precursor of the highly hydrophobic 35-amino acid metabolite, non-amyloid component (NAC) of plaques. The NAC peptide can self-aggregate into fibrils and induces aggregation of the β-amyloid peptide.

Applicants seeks to establish that abnormal synuclein expression is involved in the pathogenesis of the neurodegenerative disorders Alzheimer's disease, Parkinson's disease and Lewy Body disease as well as determining the levels of α-, β-, and γ-synuclein mRNA in the brains of Lewy Body disease, Alzheimer's disease and Parkinson's disease in correlation with clinical and pathological indicators of these diseases.

SUMMARY OF THE INVENTION

It is an object of the present invention to demonstrate the utility of β-synuclein and peptides derived therefrom as anti-amyloidogenic agents in vitro as a method for screening for amyloidogenesis and in vivo as incorporated into novel pharmaceutical compositions and treatments strategies, i.e., gene therapy and peptide infusion, for treatment of neurodegenerative disease.

It is another object of the present invention to provide methods for the use of novel transgenic animals comprising at least one transgene, portion, domain, mutant or derivative thereof that encodes a synuclein protein which is useful in screening for new anti-amyloidogenic agents.

Through the methodologies of the present invention, Applicants seek to demonstrate that a critical balance between pro- and anti-amyloidogenic molecules exists that regulates amyloid formation and cell death in Alzheimer's disease and Parkinson's disease. To this end it is postulated that β-synuclein, the non-amyloidogenic homologue of α-synuclein, is a negative modulator of α-synuclein and Aβ aggregation, having neuroprotective properties against α-synuclein and Aβ neurotoxicity and that β-synuclein and agents derived therefrom block amyloidogenesis and neurodegeneration in vivo. The established hypothesis is that β-synuclein may block Aβ aggregation either by direct inhibition of Aβ amyloidogenesis or indirectly via either α-synuclein or its 35 a.a. NAC region, inferring neuroprotective characteristics within the effected cells. Applicants seek to characterize the mechanisms by which β-synuclein blocks α-synuclein and Aβ aggregation and whether this mechanism offers protection to the cell against amyloid formation as seen in the pathologies of Alzheimer's disease and Parkinson's disease.

DETAILED DESCRIPTION OF THE PREFERRED EMBODIMENT

Figure 1:
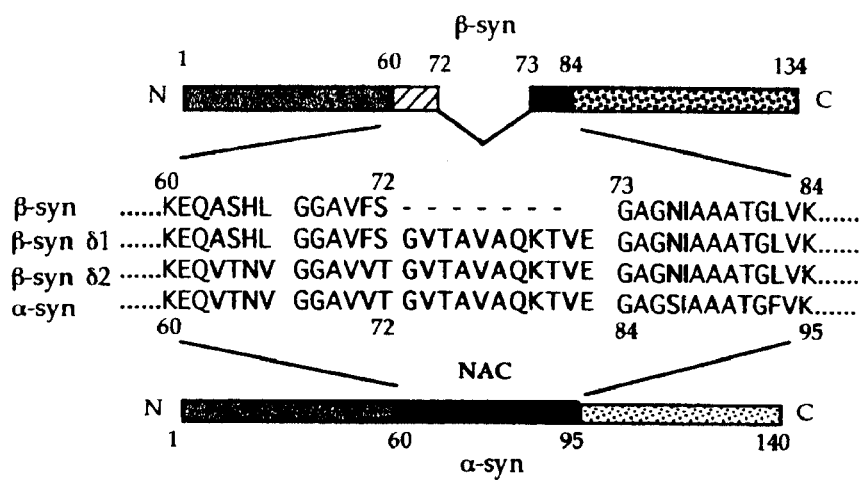
FIG. 1 is a schematic representation of β-synuclein mutants δ1 and δ2 and α-synuclein. β-synuclein lacks the part of the NAC domain corresponding to a.a. 73–83 of α-synuclein.
Figure 2:
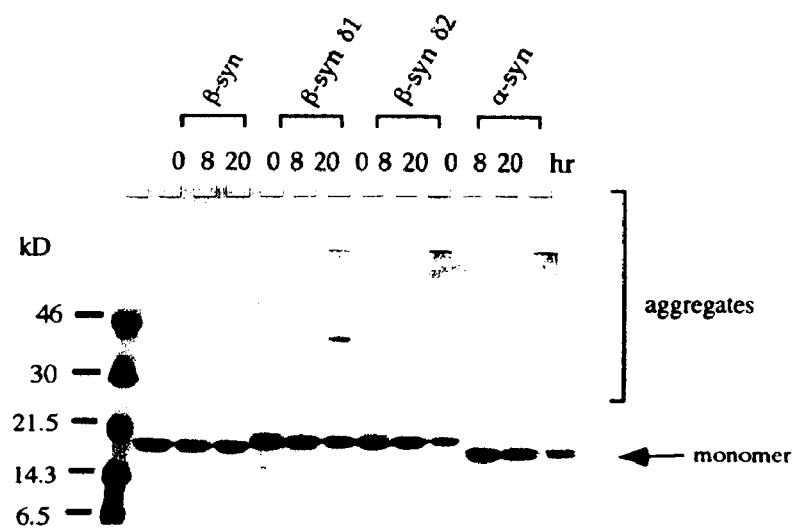
FIG. 2 shows SDS-PAGE/Coomassie brilliant blue staining results from the analysis of β-synuclein mutants δ1 and δ2 and α-synuclein incubated under high temperature conditions for the indicated times.

The mechanisms by which altered functioning of α-synuclein might lead to neurodegenerative disorders such as Alzheimer's disease, Parkinson's disease and Lewy body disease remain somewhat unclear. It is generally understood that protein aggregation is a common feature in these disorders and that α-synuclein has shown to be the major constituent of these aggregations. α-Synuclein is distinct among the various modulators of Aβ aggregation in that it is by itself an amyloidogenic protein. The amyloidogenic potential of α-synuclein is related to its 35 amino acid region denominated by the non-Aβ component of Alzheimer's disease amyloid (NAC).

α- and β-Synucleins are similar in that they share a highly conserved N-terminal region and a less conserved C-terminal acidic domain. They differ in that α-, but not β-, synuclein possesses an extremely hydrophobic amyloidogenic NAC domain. The method of the present invention will go to demonstrating that while some molecules stimulate aggregation, β-synuclein inhibits such aggregation and that the NAC domain is necessary for synuclein aggregation and amyloidogenesis both in vitro and in vivo. Additionally, the N-terminal region of β-synuclein appears to be responsible for suppressing the aggregation of α-synuclein. Using peptides derived from the N-terminal region of β-synuclein Applicants wish to establish that these peptides block α-synuclein aggregation in vitro and in vivo, thus examining the possibility that specific peptides derived from anti-amyloidogenic proteins have therapeutic potential. Demonstrating that β-synuclein and peptides derived therefrom inhibit the aggregation of Aβ and NAC in vivo will go to establishing that the anti-amyloidogenic properties of β-synuclein might be used in industrial applications for neurological research and incorporation into novel pharmaceutical compositions and strategies employing gene therapy and peptide infusion. Such utility is of special interest in understanding and combating neurodegenerative disorders such as Parkinson's disease and Alzheimer's disease.

One particularly useful application of the invention is the generation of novel transgenic animals, such as mice, to model different neurodegenerative diseases, in particular, Alzheimer's and Parkinson's Disease. Such transgenic mice will have utility in developing specific and general therapies and screening methods to identify novel anti-amyloidogenic compounds and to otherwise employ the general inventive aspects of the present invention.

Transgenic mice are achieved routinely in the art using the technique of microinjection, as described in U.S. Pat. No. 4,736,866 issued to Leder et al., and as provided by B. Hogan et al. entitled "Manipulating the Mouse Embryo: A Laboratory Manual", Cold Spring Harbor Laboratory, Cold Spring Harbor, N.Y., U.S.A. (1986). U.S. Pat. No. 5,574,206 issued to Jolicoeur particularly describes the creation of transgenic mice bearing functional HIV genes and their use in the modeling and study of HIV-mediated diseases. These references are herein incorporated by reference.

The present invention is further directed to a method for the evaluation of the in vivo effects of synuclein on amyloidogenesis and neurodegeneration through the use of such novel transgenic animals. Applicants have generated a number of transgenic mouse lines overexpressing either α-synuclein (α-syn tg and PDAPP-J9M tg) or β-synuclein (β-syn tg) to elucidate the in vivo mechanism of amyloidogenesis in Alzheimer's disease. Overexpression of α-synuclein is defined as any amount of α-synuclein that is detectable, by RPA, Western blot or like analysis, above normal α-synuclein levels found in non-transgenic littermates. The α-synuclein tg mice have been shown to express high levels of APP and Aβ in addition to exhibiting extracellular amyloidosis which, in an age- and brain region-specific manner, morphologically resembles senile plaques seen in Alzheimer's disease.

The data generated from extensive testing involving such novel transgenic animals and animal models of the present invention, specifically mice, comprising at least one transgene, portion, domain, mutant or derivative thereof, encoding α-synuclein synuclein or β-synuclein will go toward supporting and confirming their usefulness for in vivo screening for new anti-amyloidogenic agents.

Another useful application of the present invention is the generation of a cell-free system overexpressing α- or β-synuclein. The analysis of two cell lines (GT1-7 and B103) overexpressing either α- or β-synuclein suggests that α-synuclein interacts with Aβ and modulates Aβ aggregation. Because Aβ plays a central role in synaptic pathology and cell death, it is expected that synuclein may effect the neurotoxic effects of Aβ. Results have shown that α-synuclein enhances Aβ toxicity in neuroblastoma cell, whereas, β-synuclein is protective. Such data demonstrating the mechanisms through which synuclein modifies the toxic function of intracellular Aβ goes to confirming such cell systems usefulness as a method for the in vitro screening for new anti-amyloidogenic agents.

Compositions of the present invention generally comprise a therapeutically effective amount of β-synuclein or derivatives thereof as nucleic acid or gene products in a pharmaceutically acceptable carrier or excipient. Such a carrier can include, but is not limited to, saline, dextrose, water, glycerol, ethanol, or combinations thereof. The formulation of the composition should suit the desired mode of administration. Those of skill in the art are familiar with the principles and procedures discussed in widely known and available sources as Remington's Pharmaceutical Science ($17^{th}$ Ed., Mack Publishing Co., Easton, Pa., 1985) and Goodman and Gilman's The Pharmaceutical Basis of Therapeutics ($8^{th}$ Ed., Pergamon Press, Elmsford, N.Y., 1990) both of which are incorporated herein by reference.

In a preferred embodiment of the present invention, the composition comprising β-synuclein or derivatives thereof is formulated in accordance with standard procedure as a pharmaceutical composition adapted for intravenous administration to human beings and other mammals. Typically, compositions for intravenous administration are solutions in sterile isotonic aqueous buffer. Where necessary, the composition may also include a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

In cases other than intravenous administration, the composition can contain minor amounts of wetting or emulsifying agents, or pH buffering agents. The composition can be a liquid solution, suspension, emulsion, pill, capsule, sustained release formulation, or powder. The composition can be formulated as a suppository, with traditional binders and carriers such as triglycerides, such formulations being well established in the art. Oral formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a therapeutic of the present invention including encapsulation in liposomes, microparticles, microcapsules and the like.

In yet another preferred embodiment, therapeutics containing β-synuclein or derivatives thereof can be formulated as neutral or salt forms. Pharmaceutically acceptable salts include those formed with free amino groups such as those derived from hydrochloric, phosphoric, acetic, oxalic, tartaric acids and the like, and those formed with free carboxyl groups such as those derived from sodium, potassium, ammonium, calcium, ferric hydroxides, isopropylamine, thriethylamine, 2-ethylamino ethanol, histidine, procaine or similar.

The amount of the therapeutic of the present invention which will be effective in the treatment of a particular disorder or condition will depend on the nature of the disorder or condition, and can be determined by standard clinical techniques, well established in the administration of therapeutics. The precise dose to be employed in the formulation will also depend on the route of administration, and the seriousness of the disease or disorder, and should be decided according to the judgment of the practitioner and the patient's needs. However, suitable dose ranges for intravenous administration are generally about 20–4000 micrograms of active compound per kilogram body weight. Suitable dose ranges for intranasal administration are generally about 0.01 pg/kg body weight to 1 mg/kg body weight. Effective doses may be extrapolated from dose-responsive curves derived from in vitro or in vivo test systems. Those of skill in the art, applying routine pharmacological techniques, can readily determine a suitable formulation without exercising undue experimentation.

The preferred pharmaceutical composition of the present invention need not be supplied in peptide or protein form, but instead may be administered as a nucleic acid species which can then be conveniently expressed in the afflicted host. This is applicable especially for embodiments that do not lend themselves to extraneous chemical modification at the nucleotide level. For example, those of skill are well aware that certain destabilizing amino acid sequences can be introduced into a peptide by, for example, targeted protease cleavage points, such that the overall peptide is more readily degraded and does not persist to generate unwanted side effects. The converse is also true in that stabilizing amino acids may also be incorporated. U.S. Pat. No. 5,496,721 of Bachmair et al., U.S. Pat. No. 5,652,216 of Kornfelt et al., and U.S. Pat. No. 4,479,898 of Gilvarg et al. site a variety of methods by which amino acids are modified to enhance cell permeability and improve beneficial physico-chemical properties. These references are herein incorporated by reference.

In circumstances where a genetic construct, within the bounds of the invention, is capable of only transient expression, and that to the degree such expression is inadequate to completely fulfill the desired therapeutic function, additional transiently expressing constructs may be administered to supplement the action. Thus, boluses of genetic construct may be delivered, just as may boluses of recombinant and/or purified gene product for example native, modified, or synthetic protein or peptide.

In a preferred embodiment of the present invention, the genetic therapeutic may be administered directly into the individual or ex vivo into removed cells of the individual which are then reimplanted after administration of the therapeutic agent. By either route, the genetic material is introduced into cells that are present in the body of the individual. Routes of administration may include, but are not limited to, intramuscular, intraperitoneal, intradermal, subcutaneous, intravenous, intraarterial, intraoccular, and oral, as well as transdermally or by inhalation or suppository. Preferred routes of administration include intramuscular, intraperitoneal, intradermal and subcutaneous injection. Delivery of gene constructs that encode target proteins can confer mucosal immunity in individuals immunized by a mode of administration in which the material is presented in tissues associated with mucosal immunity. Thus, in some examples, the gene construct is delivered by administration in the buccal cavity within the mouth of an individual. Genetic constructs may be administered by means including, but not limited to, traditional syringes, needleless injection devices, or "microprojectile bombardment gene guns". Alternatively, the genetic vaccine may be introduced by various means into cells that are removed from the individual. Such means include, for example, ex vivo transfection, electroporation, microinjection and microprojectile bombardment. After the genetic construct is taken up by the cells, they are reimplanted into the individual. It is contemplated that otherwise non-immunogenic cells that have genetic constructs incorporated therein can be implanted into the individual even if the vaccinated cells were originally taken from another individual.

The following examples are put forth so as to provide those of ordinary skill in the art with a complete disclosure and description of how to make and use the subject invention, and are not intended to limit the scope of what is regarded as the invention.

EXAMPLE 1

Aggregation of α-synuclein is Dependent on the NAC Domain

A number of studies are providing growing evidence that the absence of the NAC domain may be responsible for the lack of amyloidogenic properties displayed by β-synuclein. Applicants confirmed this through the generation of mutants of β-synuclein having added segments of the NAC domain. The two mutants of β-synuclein were created by PCR-based site-directed mutagenesis (FIG. 1), inserting amino acids 72–83 (designated δ1)(Seq ID #1) and 63–72 (designated δ2)(Seq ID #2) of NAC and NAC N-terminal, respectively, into β-synuclein. The proteins, β-synuclein, β-synuclein δ1, β-synuclein δ2, and α-synuclein, were incubated under high temperature conditions (65° C.), according to the previously established protocol of Hashimoto et al. (Brain Res. 799: 301–306, 1998), which is herein incorporated by reference, showing that the aggregation of α-synuclein is inducible under high temperature conditions. Each of the protein samples (20 μM) was incubated under pH 6.9, 65° C. conditions for 0, 8, and 20 hours. The incubated samples were run over SDS-PAGE and the resulting protein bands visualized by Coomassie/brilliant blue staining (FIG. 2). Analysis of SDS-PAGE results indicates that both β-synuclein δ1 and β-synuclein δ2 are aggregated to form amyloid-like fibrils under high temperature conditions (using α-synuclein as an indicator of positive aggregation) whereas the wild type β-synuclein sample fails to show any formation of aggregates.

EXAMPLE 2

β-Synuclein Inhibits the Aggregation of NAC

As established in Example 1, the NAC domain of α-synuclein forms β-pleated protein structures and is present in the senile plaques of Alzheimer's disease where it may be involved in Alzheimer's disease amyloidogenesis. It can therefore be postulated that the inhibition of the aggregation of NAC might block the initial step in amyloid formation. To determine if β-synuclein acts to block NAC aggregation, 10 μM NAC was co-incubated with varying concentrations of β-synuclein (0, 1, and 10 μM) for 20 hours under the same high temperature conditions (data not shown) as described previously in Example 1. The study establishes that co-incubation with β-synuclein inhibits the aggregation of NAC in a concentration-dependent manner.

EXAMPLE 3

Assay for Synuclein mRNA Expression

DNA templates for human synuclein and actin riboprobes were generated from total RNA extracted from human neocortex by reverse transcriptase polymerase chain reaction (PT-PCR), a technique known to those in the art. Three pairs of oligonucleotide primers complimentary to human (h) synuclein genes were used to amplify DNA templates complimentary to the following sequences: a) h α-synuclein nucleotides 53–475 (Seq ID #3); b) h β-synuclein nucleotides 55–303 (Seq ID #4); c) h γ-synuclein nucleotides 49–258 (Seq ID #5); and d) β-actin nucleotides 480–559 (Seq ID #6). Amplification products were subcloned into pCRII (Invitrogen, La Jolla, Calif.) and T7 or SP6 RNA polymerase (Ambion, Austin, Tex.) was used to generate $^{32}$P-labeled antisense riboprobes from 100 ng of linearized plasmids.

Total RNA was isolated from snap-frozen brain tissue using the TRI Reagent (Molecular Research Center, Cincinnati, Ohio). For comparison of RNA levels among the 43 cases studied, samples from the superior temporal cortex were used. Additional studies of synuclein mRNA expression in the normal brain was performed with snap-frozen tissues from the midfrontal, superior temporal, inferior parietal, occipital, hippocampus, cerebellum, basal ganglia and substantia nigra of three control cases. The quality of human postmortem tissues was assessed by electrophoresis on agarose-formaldehyde gels and densiometric comparisons of 28S and 18S ribosomal RNA bands. Levels of specific RNAs were determined using solution hybridization ribonuclease protection assay (RPA), the technique known to those of skill in the art. Briefly, 10 μg of RNA hybridized to 32P-labeled anti-sense riboprobes was digested with 40 U/ml RNase T1 (GIBCO/BRL, Grand Island, N.Y.) and 20 μg/ml RNase A (Sigma Chemical Co., St. Louis, Mo.) in 100 μl volume of digestion buffer. RNase was then inactivated with Proteinase K/N-laurylsarkosine and precipitated with 4-guanidine thiocyanate/0.5% N-laurylsarkosine and isopropanol. Samples were separated on 5% acrylamide/8M Urea TBE gels using known protocols. Dried gels were exposed to Biomax® film (Kodak, Rochester, N.Y.) and signals were quantitated with a PhosphorImager SF (Molecular Dynamics, Sunnyvale, Calif.) using the ImageQuant software and expressed as integrated pixel intensities over defined volumes. Final values were expressed as ratios of (specific signal-background)/(actin signal-background) to correct for differences in RNA content/loading across samples. For comparisons of signals representing distinct probes, readings were corrected for the differences of specific activities and the number of uridine nucleotides contained in each fragment. Once corrections for RNA loading and amount of radioactive label were completed, values for each of the synucleins were added to total synuclein mRNA levels and then the proportional percentage of each of the synucleins to the total was determined. Results were confirmed in at least two independent RPAs.

Statistical analysis of RPA results demonstrates that levels of synuclein expression vary from high in the neocortex to low in the substantia nigra. This is significant as vulnerability to the pathogenic process associated with Alzheimer's disease and Lewy Body disease might depend on the patterns of synuclein expression in various regions of the brain. RPAs for α-, β-, and γ-synuclein identifies bands at 423 bp, 249 bp and 210 bp respectively. PhosphorImager analysis shows that the highest levels of synuclein expression can be observed in the neocortex, followed by the hippocampus and cerebellum, while the lowest levels are detected in the basal ganglia and substantia nigra. Upon estimating the proportion of each of the three synucleins as a percentage of the total signal, β-synuclein comprises approximately 75–80% of the total message of synucleins, followed by γ-synuclein (10–15%) and α-synuclein (8–10%). The relative proportions are conserved across the neocortex and cerebellum, while in the hippocampus, the tendency is toward a higher proportion in γ-synuclein expression. In the basal ganglia, α-synuclein expression is the highest and in the substantia nigra both β- and γ-synuclein expression show the greatest levels of expression.

These and other studies are consistent in showing that, during neuronal development, levels of synuclein expression are the highest throughout the cortex and that this expression can be correlated with synaptogenesis. Studies of the adult rat brain also show that the levels of synuclein immunoreactivity is the highest in the neocortal regions of the brain followed by the hippocampus and cerebellum and are the lowest in the brainstem and subcortal regions. This is of particular interest especially in view of the fact that the substantia nigra is an area particularly vulnerable to the pathogenic process in Lewy Body disease. Establishing a defined pattern of synuclein expression in the brain is a critical step in the design of therapeutic agents for the inhibition of the synucleins that facilitate aggregation.

Figure 3:
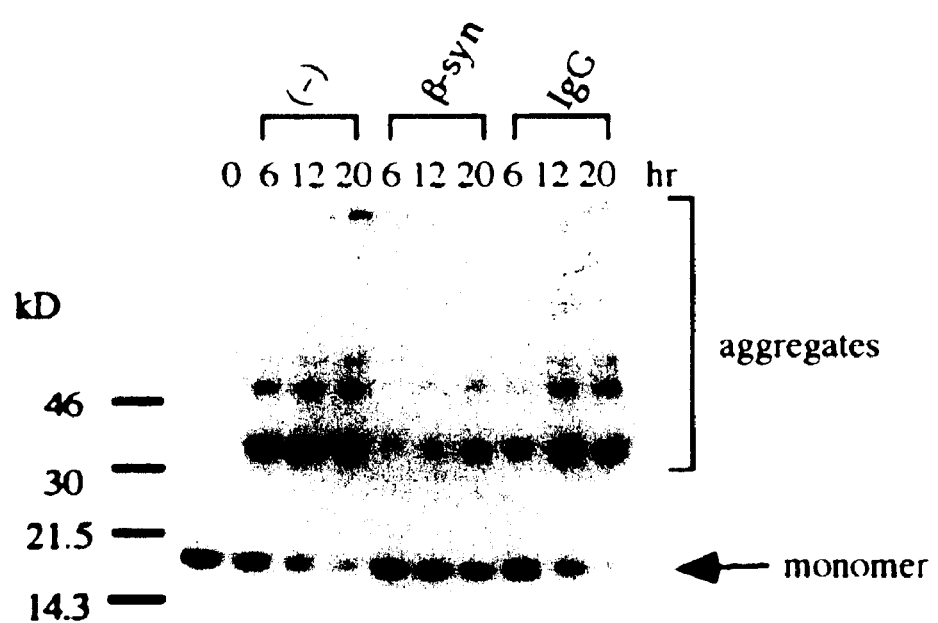
FIG. 3 shows SDS-PAGE/Coomassie brilliant blue staining results of the incubation of α-synuclein alone or in the presence of either β-synuclein or IgG under high temperature conditions for the indicated times.
Figure 4:
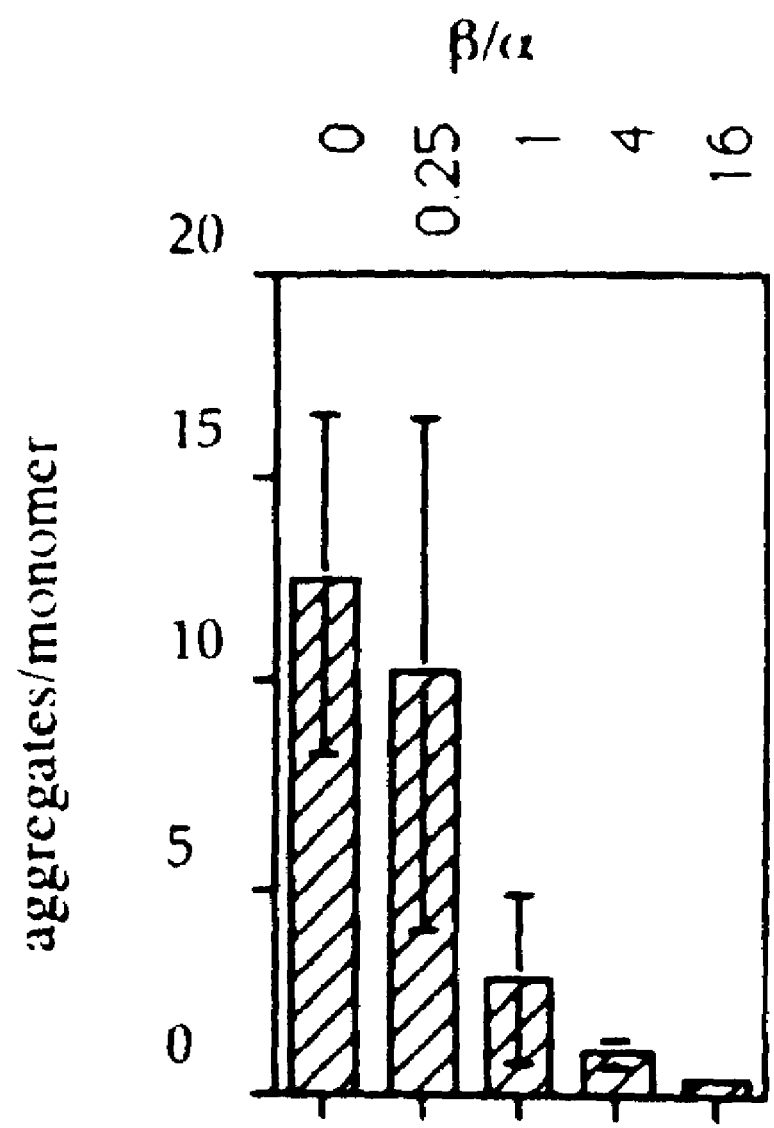
FIG. 4 shows a graph generated from the quantification of data of the ratio of β-synuclein and α-synuclein aggregates (aggregation) versus monomers (non-aggregation)

EXAMPLE 4

β-synuclein and Peptides Derived Therefrom Inhibit the Aggregation of α-synuclein For the purpose of demonstrating that β-synuclein acts as a negative modulator of the aggregation of α-synuclein, 10 μM of β-synuclein was co-incubated with 10 μM α-synuclein under high temperature conditions, similar to those as previously described in Example 1, and its effects on aggregation was assessed by immunoblotting analysis (FIG. 3). Briefly, 10 μM α-synuclein was incubated either alone, or in the presence of either 10 μM β-synuclein or 10 μM IgG under pH 6.9 buffer conditions at 65° C. for 0, 6, 12, and 20 hours. In a simultaneous experiment, 10 μM α-synuclein was incubated with various concentrations (0, 2.5, 10, 40, and 160 μM) of β-synuclein under the same pH and temperature conditions for 20 hours. Quantification of immunoblotting analysis showing the ratio of aggregates versus monomer can be seen in FIG. 4. Results indicate that β-synuclein inhibits α-synuclein aggregation in a dose dependent manner and more than equi-molar concentrations of β-synuclein are shown to be effective.

Figure 5:
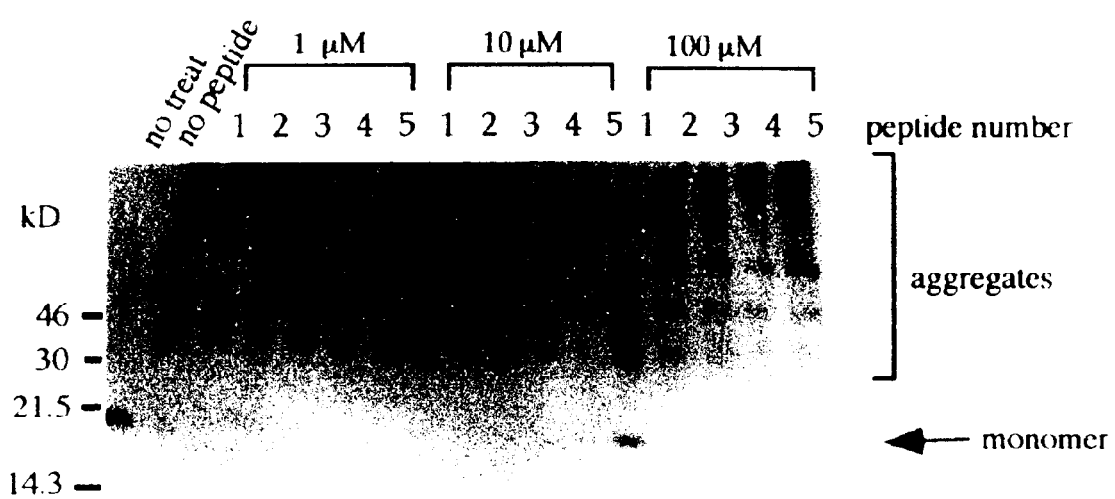
FIG. 5 shows the immunoblotting analysis of varying concentration of the synthetic peptide corresponding to a.a. 1–15 of β-synuclein inhibiting α-synuclein.

Because synuclein forms both homo- and hetero-dimers, it is likely that binding might occur in the vicinity of the N-terminus. To characterize the functional domain of β-synuclein responsible for suppression of α-synuclein aggregation, peptides corresponding to amino acids 1–15 (Seq ID #7), 16–27 (Seq ID #8), 28–38 (Seq ID#9), 39–50 (Seq ID #10), and 51–61 (Seq ID #11) of the N-terminal region of β-synuclein were synthesized. Varying concentration of the peptides (1, 10, and 100 μM) were co-incubated with 10 μM α-synuclein under high temperature conditions for 20 hours. Immunoblotting analysis (FIG. 5) showed that only one peptide, corresponding to aa 1–15 of β-synuclein, inhibited α-synuclein in a dose dependent manner. This result suggests that this region of β-synuclein may be regarded as a therapeutic agent to block α-synuclein aggregation.

EXAMPLE 5

A Peptide Derived from β-synuclein Inhibits the Interaction Between α-synuclein and Aβ

Figure 6:
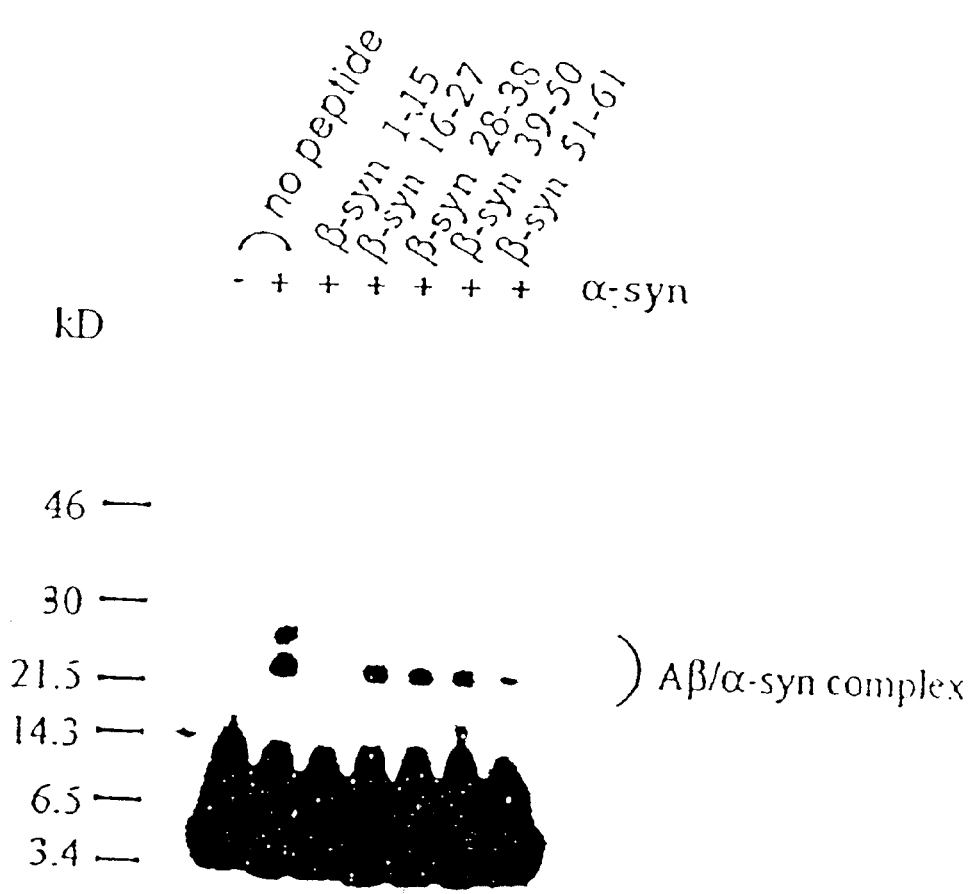
FIG. 6 shows the immunoblot analysis of synthetic peptides corresponding to a.a. 1–15 and 51–61 of β-synuclein suppression on the formation of the Aβ and α-synuclein complex.

While the results of experiments discussed in Example 4 have established that β-synuclein and peptides derived therefrom are capable of inhibiting the aggregation of α-synuclein, there still remains the question as to by what mechanism of action can inhibition be attributed. Those in the art generally agree that β-Synuclein blocks Aβ protofibril formation by one of two possible mechanistic pathways. In the first pathway, inhibition is facilitated through indirectly blocking NAC or α-synuclein interaction with Aβ. In the second possible pathway, inhibition is facilitated by the direct blocking Aβ aggregation. To test the possibility that the first pathway is the mechanism which initiates fibrillar formation, 10 μM α-synuclein and 10 μM Aβ1-40 were co-incubated with 100 μM of each of the 5 synthetic β-synuclein peptides previously described in Example 4. Immunoblotting analysis resulted in two of the synthetic peptides, corresponding to the β-synuclein amino acid regions 1–15 (Seq ID #7) and 51–60 (Seq ID #11) showing significant suppression of the formation of SDS-resistant complexes of α-synuclein and Aβ1-40 (FIG. 6).

EXAMPLE 6

The Overexpression of α-synuclein and β-synuclein in Mammalian Cell Systems (in vitro)

To investigate the pathophysiological effects of synuclein in vitro, two types of stable cells lines were established, using known protocols, overexpressing either α- or β-synuclein.

In GT1-7 murine hypothalamic neuronal cells, overexpression of α-synuclein resulted in elevated mitochondrial dysfunction and oxidative stress as compared to non-transfected controls, implicating α-synuclein as having a major role in the regulation of mitochondrial function. To determine if the overexpression of α-synuclein causes dysregulated neuronal function, GT1-7 cells were transfected with the mammalian expression vector pCR3.1 (Invitrogen) using standard transfection protocols well known in the art. The cells were transfected with or without insertion of murine α-synuclein cDNA. The resulting expression of α-synuclein was measured at both mRNA and protein levels using RPA and immunoblotting analysis. Clones which either overexpressed or underexpressed α-synuclein (via transfection with an anti-sense plasmid) were selected and analyzed. The study shows that α-synuclein overexpression facilitates mitochondrial alterations accompanied by an increase in the level of free radical moieties, as evidenced by 2'-7'-dichlorofluoroscein loading, increased levels of glutathione, and decreased secretion of gonadotropin-releasing hormone. These alterations were ameliorated by pretreatment with the anti-oxidant, vitamin E. Furthermore, α-synuclein overexpression in GT1-7 cells results in the formation of α-synuclein—immunopositive inclusion-like structures. GT1-7 cells transfected with β-synuclein did not show any significant alterations.

In the second cell system, B103, it was demonstrated that the altered expression of synuclein affected cell adhesion and neurite extension. B103 cells were transfected with the mammalian expression vector pCR3.1 (Invitrogen) with or without insertion of human α-synuclein or β-synuclein cDNA. The expression of α-synuclein was determined at both mRNA and protein levels by RPA and immunoblotting analysis. Under 10% serum conditions, α-synuclein overexpressing cells were observed to be round in shape, whereas the cells overexpressing β-synuclein were of a more flattened shape, compared to that of the vector-transfected cells. This difference in cell morphology may be due to alterations in cell adhesion properties. Adhesion assays revealed that, compared to the control cells, the β-synuclein transfected cells had greater adhesivity while the α-synuclein transfected cells demonstrated a lesser amount of adhesion. Additionally, under serum-free assay conditions, after 24 hours, neurite outgrowth in the α-synuclein overexpressing cells was significantly shorter than that of the control cells, while neurite extension in β-synuclein overexpressing cells was only slightly shorter than the control cells. Because anti-oxidants like catalase (100 μg/ml), superoxide dismutase (100 U/ml) and vitamin E (500 μM) demonstrate little effect, it is likely that oxidation is not involved in these overexpression mechanisms. These results clearly demonstrate that α-synuclein and β-synuclein differently regulate cell adhesion and altered synaptic plasticity in vivo.

Based on the results of this study, it is shown that β-synuclein has inhibitory properties and consistently ameliorates Aβ cytotoxicity. When B103 neuroblastoma cells were incubated with Aβ (20 μM) under serum-free conditions for three days, dead cells become prominent due to the cytotoxic effects of Aβ. Contacting the cells with β-synuclein (20 μM) blocked the effects of this cytotoxicity, whereas, contact with α-synuclein (20 μM) demonstrated to be detrimental to cell survival in vivo.

EXAMPLE 7

Figure 7:
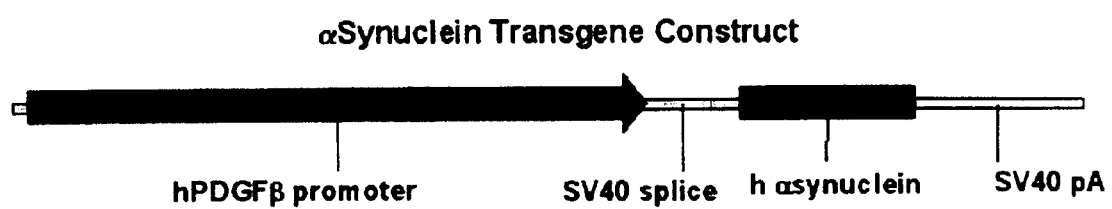
FIG. 7 shows the schematic of the human PDGF-β promoter driven transgene encoding wild-type human α-synuclein containing SV40 intron and SV40 poly A.

The Generation of Transgenic Mice Overexpressing Human α-synuclein to Evaluate the Role of Accumulated α-synuclein in the Pathogenesis of Neurodegenerative Disorders Two novel lines of transgenic mice overexpressing α-synuclein were generated to mimic some aspects of Parkinson's disease and Alzheimer's disease pathology. Following the protocol of Mucke et al., ("Protection against HIV-1 gp120-induced brain damage by neuronal overexpression of human amyloid precursor protein (hAPP)", J.Exp.Med. 181: 1551–56 (1995)), which is herein incorporated by reference, the first mouse line was developed which expressed human amyloid precursor proteins, APP770, 751 and 695, bearing the Swedish (K670N, M671N) and Indiana (V717F) mutations under the control of the platelet derived growth factor β (PDGF-β) promoter. This mouse model was denominated PDAPP-J9M. The second model, denominated α-synuclein tg expressed wild-type human α-synuclein also under the regulatory control of the platelet-derived growth factor β (PDGF-β) promoter. This particular promoter was chosen because it has been successfully used to target the expression of other human proteins to neurons in transgenic models of neurodegenerative disease (Games et al., "Alzheimer-type neuropathology in transgenic mice overexpressing V717F β-amyloid precursor protein"; Nature 373; 523–27, 1995) and is herein incorporated by reference. Human α-synuclein cDNA was prepared by PCR using pfu Taq polymerase (Stratagene, La Jolla, Calif.) with a HBS6-1 plasmid as a template. The PCR product was subcloned into a pBluescript by TA cloning, and the fidelity of the nucleotide sequence was confirmed as 100% by dideoxy sequencing. Subsequently, the NACP cDNA fragment was subcloned into pCEP4 mammalian expression vector (Invitrogen). Because it has been suggested that genomic constructs are more efficiently expressed in transgenic mice than constructs that are identical except for the lack of introns, an intron was inserted between the PDGF-β promoter and α-synuclein cDNA in order to obtain a high level of mRNA expression. The mammalian cell promoterless reporter vector pNASSβ was used, allowing for cloning of the promoters utilizing the β-gal expression and containing the SV40 intron before the β-gal cDNA sequence (Clonetech). First, PDGF-β promoter derived from the XbaI-SalI fragment of psisCAT (Dr. Tucker Collins, Harvard Medical School) was subcloned into the EcoRI/XhoI site of pNASSβ using an EcoRI-XbaI linker. After the first subcloning, the segment containing the β-gal cDNA and polyA signal in the resulting plasmid was substituted with the NotI/SalI fragment of the pCEP4-α-synuclein which encodes α-synuclein cDNA plus SV40 polyA cDNA. Thus, the expression vector, PSNS, which contains PDGF-β promoter, SV40 intron, α-synuclein cDNA and SV40 polyA was constructed (FIG. 7).

Figure 8:
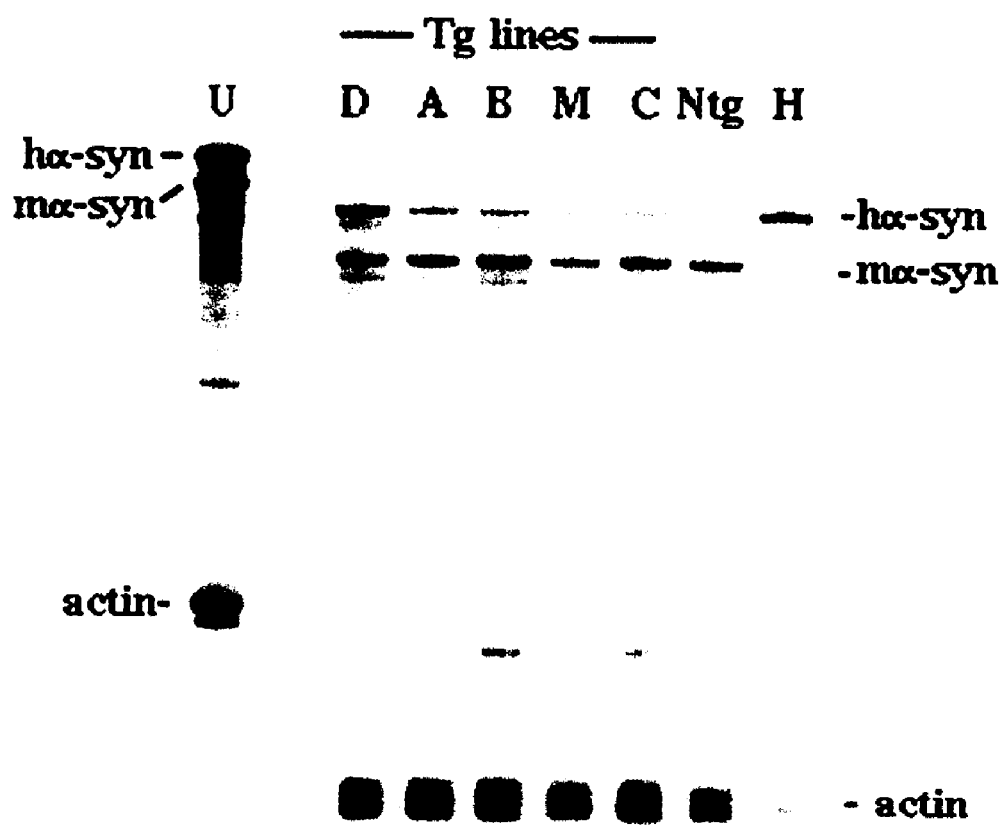
FIG. 8 shows a representative radiograph of cerebral α-synuclein mRNA levels in transgenic (Tg) mice of different lines, a non-transgenic (Ntg) mouse, and human (H) without neurological disease. The left-most lane shows signals of undigested (U) radio labeled RNA probes.

The resulting fusion gene was freed of vector sequences, purified and microinjected using standard protocols into one-cell embryos of the cross C57BL/6×DBA/2 $F_2$ mice. Thirteen transgenic founders ($F_0$) were identified as having the transgenic sequence integrated into the genome by slot-blot analysis of tail DNA and subsequently crossed with wild-type C57BL/6×DBA/2 $F_1$ mice to establish the transgenic lines. The resulting $F_1$ generation from each line was screened by PCR using the tail DNA. Briefly, genomic DNA was extracted using the protocol of Miller et al. (Nucleic Acids Research 16(3), 1215, 1988). PCR was run at 30 cycles: 93° C.×30 seconds, 57° C.×30 seconds, 72° C.×1.5 minutes, 72° C.×5 minutes, using sense (Seq ID #12) and anti-sense (Seq ID #13) primers. A subset of the positive mice from the $F_1$ generation were sacrificed in order to make an analysis of the levels of mRNA using ribonuclease protection assay and levels of protein expression using Western blot analysis, both procedures well known to those in the art. For the ribonuclease protection assay, the α-synuclein/SV40 riboprobe was generated by PCR using primers located in the PDGF-α-synuclein transgene. The sense primer is a 20 mer starting at nucleotide 194 of the α-synuclein (Seq ID #12). The antisense primer is a 21 mer starting at nucleotide 270 of the SV40 poly A signal of pCEP4 vector (Invitrogen) (Seq ID #13). This poly A signal was used to construct the PDGF-α-synuclein transgene. The riboprobe is 420 nucleotides in length and is also capable of detecting murine α-synuclein at approximately nucleotide 100. As a loading control, an actin riboprobe was used which detects a 79 base pair fragment and is from base pairs 480–559 (Seq ID #6). This probe recognizes both murine and human actin mRNA fragments. Ribonuclease protection assay blots (FIG. 8) were imaged with a PhosphorImager (as previously described in Example 1) and quantified using the ImageQuant software. Levels of expression of α-synuclein were corrected for actin expression levels.

Figure 9:
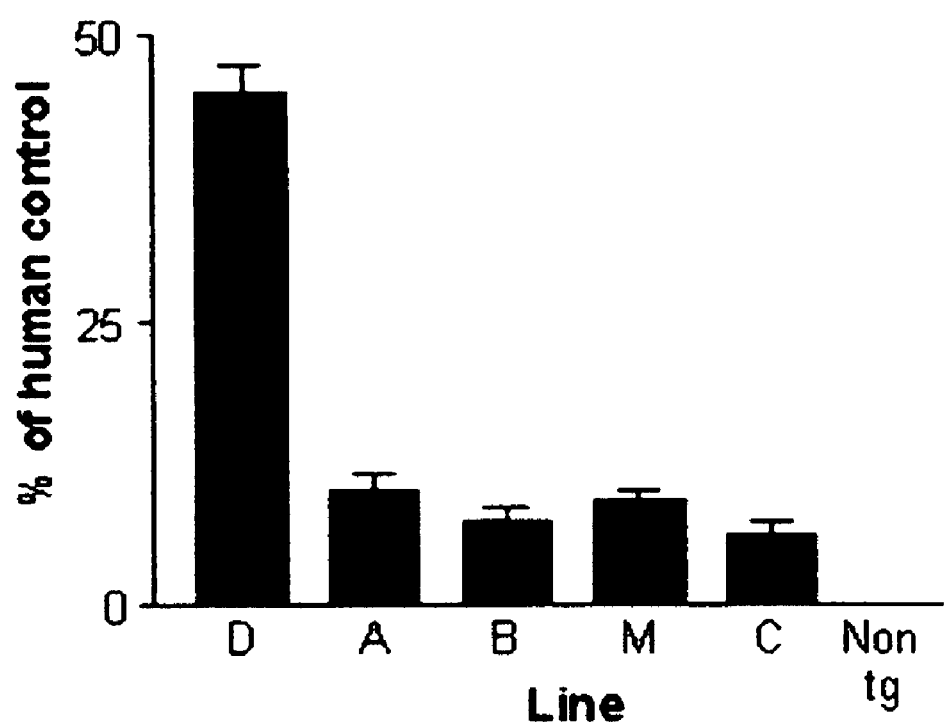
FIG. 9 shows quantified PhosphorImager analysis of human α-synuclein mRNA signals (expressed as percent human control). Bars represent means±SEM.

After this screening step, mouse lines were selected according to expression levels and breeding was continued. High, intermediate and low expression lines were selected. The highest level of transgene expression was detected in mice from the line designated D (n=3). Intermediate and low levels of expression were observed in the lines designated M, A, B and C (n=3 for each line) respectively. No human α-synuclein signal was detected in the nontransgenic line of mice (n=4) used as a control. FIG. 9 shows the quantitated plot for each expression line from the ribonuclease protection assay data.

Figure 10:
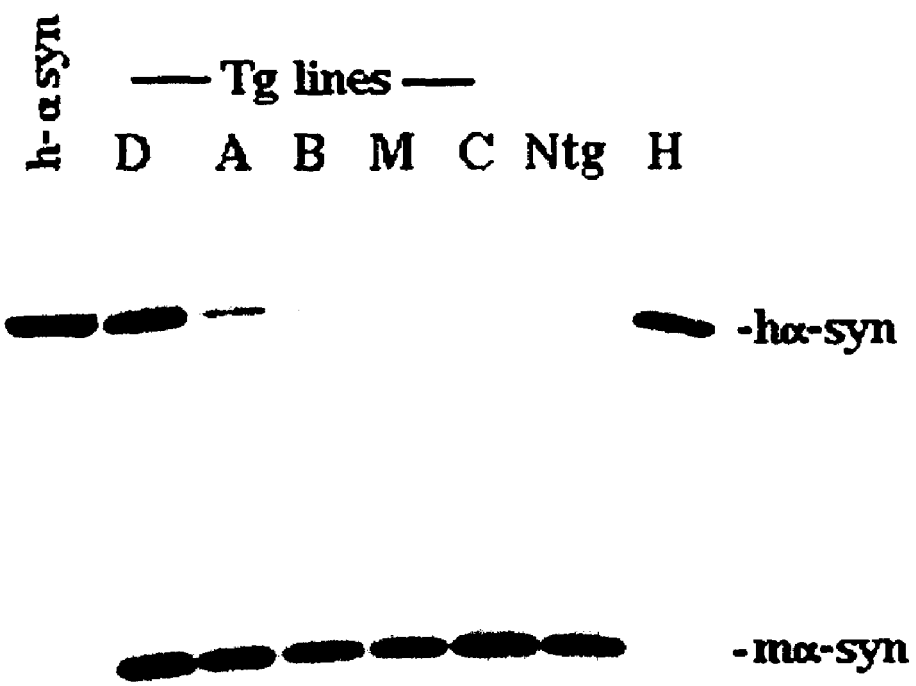
FIG. 10 shows Western blot analysis of protein with affinity-purified human- and mouse-specific α-synuclein antibodies. The human-specific antibody is recognized as a 19-kD band.
Figure 11:
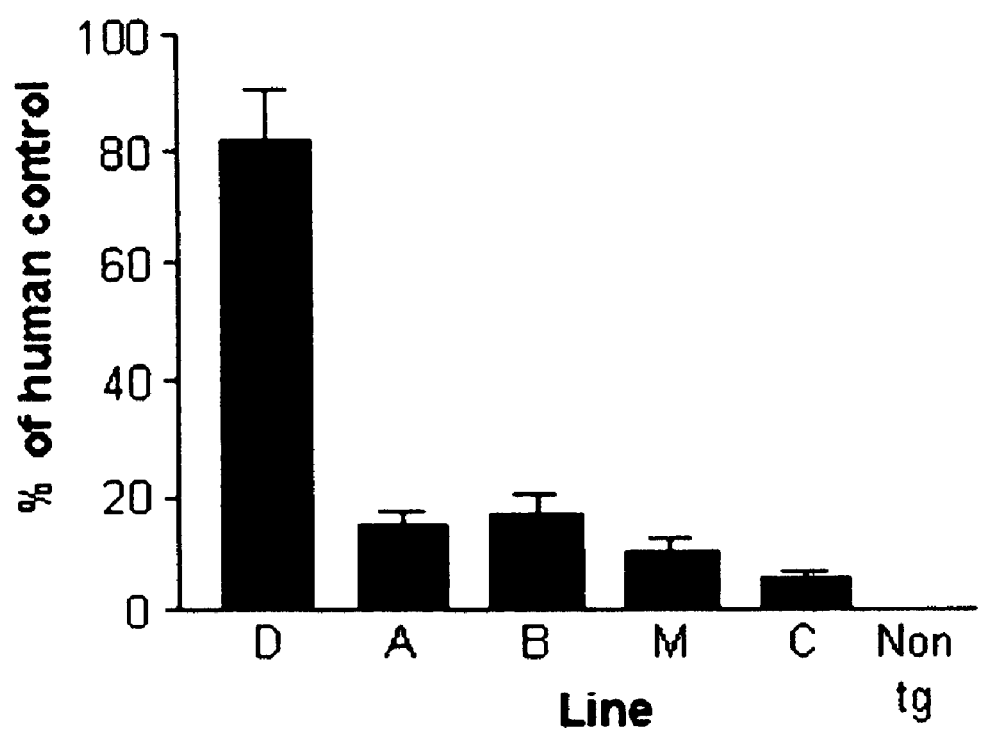
FIG. 11 shows PhosphorImager analysis of human α-synuclein signals (background values subtracted) from semi-quantitative Western blots of human α-synuclein expression in tg mice lines. Results were expressed as percent immunoreactivity of normal human control. Bars represent means±SEM.

Western blot analysis (FIG. 10) of the various mouse lines, using affinity-purified human specific antibody, recognized a 19-kD band, consistent with human α-synuclein, in both the transgenic mice and the human control. Only minimal cross-reactivity with mouse α-synuclein was seen in nontransgenic mice. In contrast, the murine-specific antibody recognized endogenous α-synuclein in transgenic and nontransgenic mice, with only a faint band noted in the human control. PhosphorImager analysis (FIG. 11) of human α-synuclein signals from the semiquantitative Western blot revealed the highest levels of human α-synuclein expression in mice from line D (n=3). Intermediate to low levels of expression were seen in mice from the lines M, A, B, and C (n=3 for each line). The signal obtained in the nontransgenic mouse control (n=4) was considered background. The results were expressed as percent immunoreactivity of the normal human control (n=3).

EXAMPLE 8

The Effects of α-synuclein Overexpression in Neuronal Cells

To characterize the effects of human α-synuclein expression in neurons, transgenic mice form the various expression lines A (n=6), B (n=8), C (n=17), D (n=15), and M (n=6) were compared with age-matched nontransgenic controls. By two months of age, transgenic mice from all lines had prominent intraneuronal inclusions (nuclear and cytoplasmic) that were strongly immunoreactive with antibodies to human, but not mouse α-synuclein (results not shown). The antibody to human α-synuclein also recognized the characteristic intracytoplasmic inclusions found in Lewy body disease. Human α-synuclein-immunoreactive inclusions were most abundant in transgenic mice from the highest expression line D, and were not detected in any of the nontransgenic controls. in the transgenic mice, the inclusions were most frequently evident in the neurons in the deeper layers of the neocortex, the CA3 region of the hippocampus, and the olfactory bulb and occasionally in the substantia nigra (results not shown). These regions of the brain are also typically effected in patients suffering from Lewy body disease.

Degeneration of dopaminergic neurons in the substantia nigra results in Parkinson's disease and is frequently preceded by the formation of Lewy bodies. To assess whether these cells develop human α-synuclein-positive inclusions in the effected transgenic mice, brain sections were double-immunolabled with antibodies to human α-synuclein and tyrosine hydroxylase (TH), which is necessary for the synthesis of dopamine in the brain. Results (not shown) indicated that neurons showing a positive reactivity with TH also displayed abnormal accumulations of α-synuclein, consistent with observations in humans with Lewy body disease. The neuronal inclusions evident in the transgenic mice were accompanied by occasional human α-synuclein-immunoreactive neuritic processes.

Electron microscopic analysis was used to characterize the ultrastructural features of the human α-synuclein-positive neuronal inclusions observed in the various transgenic mouse lines. In contrast to the nontransgenic controls displaying normally appearing neuronal structure, neurons of the high-expression human α-synuclein mice showed electron-dense deposits of 0.1 to 0.25 μm in diameter associated with the rough endoplasmic reticulum. Larger electron-dense deposits of 0.5 to 1 μm in diameter were observed in the neuronal nuclei of the high-expression transgenic mice. A study by Davies et al. (Cell 90:537–548, 1997), which is herein incorporated by reference, has demonstrated that other synaptic proteins also accumulate in the neuronal nuclei in other neurodegenerative conditions. For instance, fibrillar aggregates of huntington are found in huntington transgenic mice as well as in patients with Huntington's disease.

In 9- to 11-month old α-synuclein transgenic mice, larger electron-dense cytoplasmic inclusions, 2 to 5 μm in diameter, were identified that were composed of fine granular material and contained clear vacuoles, 50 to 100 nm in diameter, but no fibrillar elements. Immunogold electron microscopic analysis, a technique well known to those in the art, confirmed that the cytoplasmic inclusions contained human α-synuclein immunoreactivity. Control experiments in which sections from transgenic mice were incubated in the absence of primary antibody showed no immunogold labeling associated with the observed inclusions. Large nuclear or cytoplasmic inclusions, such as those found in the high-expression transgenic lines, were not observed in non transgenic controls or transgenic mice expressing other amyloidogenic proteins directed by the same promoter.

EXAMPLE 9

Analysis of Dopaminergic and Motor Deficits in α-synuclein Transgenic Mice Having High Numbers of Neuronal Inclusions The cytoplasmic neuronal inclusions observed in the various transgenic mouse line of Examples 1–3 resemble, in many respects, Lewy bodies observed in humans afflicted with Parkinson's disease. Similarities include the location of neuronal inclusions in the deep layers of the neocortex and in dopaminergic neurons of the substantia nigra. There are also similarities with respect to the level and type of reactivity observed with antibodies raised against human α-synuclein or ubiquitin. However, the neuronal inclusions observed in the α-synuclein transgenic mice differ from Lewy bodies in that they are less circumscribed, are present in the nucleus, and lack the formation of fibrillar components. It is unclear why no fibrillar structures were detected in association with the electron-dense inclusion in transgenic mice like those evaluated in Example 3. It has been proposed that additional stress conditions, resulting in the formation of oxygen-free radicals, are necessary to promote fibrillar aggregation of human α-synuclein. This condition is similar to that encountered in human APP transgenic mice where there is no formation of neurofibrillary tangles or paired helical filaments despite extensive amyloid deposition.

Figure 12:
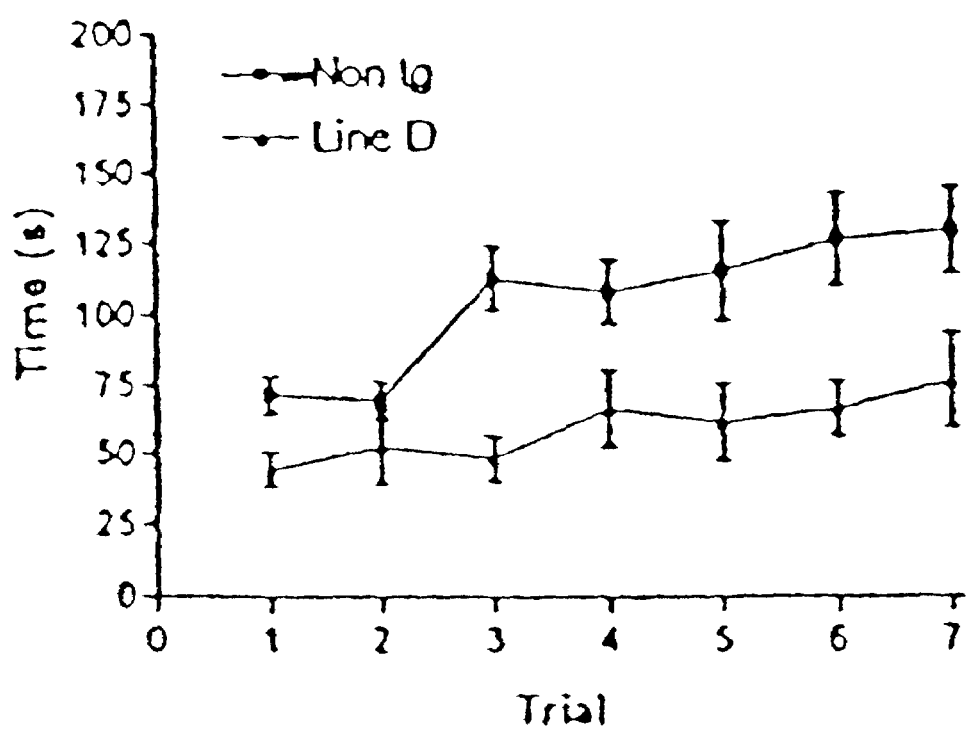
FIG. 12 shows resultant graph of rotorod testing in 12-month-old transgenic mice from the highest expressor line (line D) compared to non-transgenic littermates. Testing revealed a significant decrease in motor performance for tg mice expressing α-synuclein. All quantitative data represent group means±SEM.

Motor deficits in Lewy body disease are associated with degeneration of the nigral dopaminergic neurons projecting to the striatum. To determine if loss of dopaminergic input to the striatum in transgenic mice is associated with Parkinson's disease related neurological impairments, mice were examined with a rotorod test, a behavioral testing mechanism well known to those familiar with such procedures. In comparison with nontransgenic littermate controls, transgenic mice from the high-expression line D showed significant deficits in motor performance (FIG. 12). The loss of dopaminergic terminals and motor abnormalities in human α-synuclein transgenic mice demonstrates that intraneuronal accumulation of amyloidogenic synaptic proteins can elicit morphological and functional impairments of the central nervous system. The dopaminergic and behavioral deficits were detected only in the high expression line and not in low-expression lines. While the highest-expression lines clearly had more human α-synuclein and ubiquitin immunoreactive neuronal inclusions than the other transgenic lines, these inclusions were observed in all the transgenic lines evaluated. This may lead to the conclusion that a critical threshold of α-synuclein accumulation is required for dopaminergic and behavioral deficits to become detectable. None-the-less, the evaluation of such neurophysiological characteristics, as previously described, are well known to those of skill in such evaluations. As such, it is apparent that the increased expression of wild-type α-synuclein plays a key role in the pathogenesis of neurodegenerative conditions associated with amyloidogenesis.

EXAMPLE 10

Generation of Transgenic Mouse Line Overexpressing β-synuclein

Figure 13:
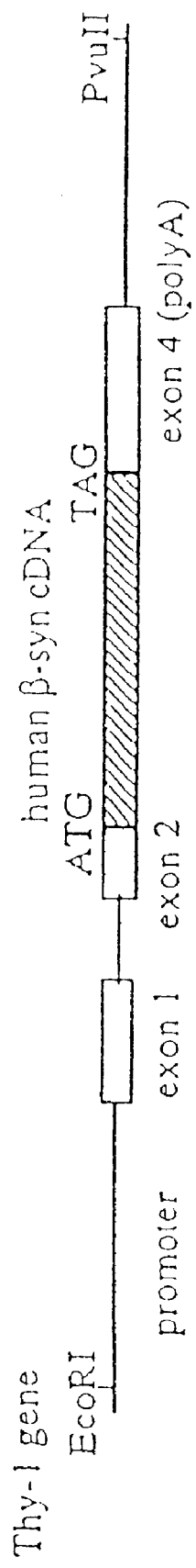
FIG. 13 shows the schematic of the transgenic construct for β-synuclein in the Thy-1 gene cassette.

The mThy-1 expression cassette was used to generate transgenic mice overexpressing human β-synuclein. This cassette contains the EcoRi fragment of the mouse Thy-1 gene ligated in the Pvull fragment of pUC18. A Banl-XhoI fragment of the mThy-1 gene (exon 2 to exon 4) was replaced by an XhoI site containing the gene of interest. A 404 nucleotide human β-synuclein cDNA fragment (Genebank # S69965) was generated by RT/PCR from human brain mRNA with a 5' SalI and 3' XhoI sites added. The PCR fragment was ligated into PCRII (Invitrogen) and sequenced for accuracy. Subsequently, the β-synuclein fragment was released by SalI/XhoI digestion and then ligated into the XhoI site of the Thy-1 expression cassette (FIG. 13). The resulting fusion gene was freed of vector sequences, purified and microinjected into one cell embryos (C57Bl/6xDBA/2F1) according to standard protocol. Five transgenic founders were identified by PCR analysis of tail DNA and subsequently bred with C57BL/6xDBA/2F1 mice to establish the transgenic line overexpressing β-synuclein. Transgenic offspring were identified by PCR of tail DNA. Briefly, genomic DNA was extracted and amplified in 35 cycles (93° C.×30 sec, 49° C.×30 sec, 72° C.×60 sec) with a final extension at 72° C.×5 min. A 35 bp sense primer 5'-CCGGTCGACCGCCACCATGGAC-GTGTTCAT-GAAGG-3' (Seq ID #14) and a 31 bp antisense primer 5'-CCGCTCGAGCCTACGCCTCTGCTCATACTCC-3' (Seq ID #15) were used to generate the β-synuclein fragment and screen the offspring. preferred embodiments, the vaccines contain about 0.1 to about 500 micrograms of DNA. In other preferred embodiments, the vaccines contain about 1 to about 350 micrograms of DNA. In still other preferred embodiments, the vaccines contain about 25 to about 250 micrograms of DNA. In yet other preferred embodiments, the vaccines contain about 100 micrograms DNA. These ranges are useful as crude guidelines only and will vary according to many factors, as one of skill is aware.

The genetic vaccines according to the present invention are formulated according to the mode of administration to be used. One having ordinary skill in the art can formulate a genetic vaccine or therapeutic that comprises a genetic construct.

In cases where intramuscular injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers may be utilized and include gelatin and albumin. In some embodiments, a vasoconstriction agent is added to the formulation. The pharmaceutical preparations according to the present invention are preferably provided sterile and pyrogen free.

EXAMPLE 14

Therapy by Administration of Purified Proteins

Protein purification has been made routine by the use of various short peptide tags that can be fused to the protein of interest at the nucleic acid level to facilitate protein purification via affinity chromatography directed against the tag. Such tags can be conveniently removed or, alternatively, left intact without normally effecting protein function. Many different tags exist and are embraced within the scope of this invention.

For example, the Flag octapeptide (Hopp et al., Bio/Technology 6:1204, 1988, offered through Kodak, New Haven, Conn.) can be positioned at the N-terminus and does not alter the biological activity of fusion proteins. Additionally, the tag is highly antigenic and provides an epitope reversibly bound by a specific monoclonal antibody, enabling rapid detection and purification of the expressed fusion protein. The sequence is also specifically cleaved away by bovine mucosal enterokinase. A murine monoclonal antibody that binds the Flag sequence has been deposited with the ATCC under accession number HB 9259. Methods of using the antibody in purification of fusion proteins comprising the Flag sequence are described in U.S. Pat. No. 5,011,912, which is incorporated by reference herein.

Other types of linkers that can be used include, but are not limited to maltose binding protein (NBP), glutathione-S-transferase (GST), thioredoxin (TRX) and calmodulin binding protein (CBP). Kits for expression and purification of such fusion proteins are commercially available from such companies as New England BioLabs (Beverly, Mass.), Pharmacia (Piscataway, N.J.), Invitrogen (Carlsbad, Calif.) and Stratagene (San Diego, Calif.), respectively.

In order to assure full functionality and structure conformation of the fusion protein incorporating the composition of the present invention, it may be necessary to add between the individual portions of the hybrid protein a "linker" or "spacer" as is known in the art. Suitable linker sequences will adopt a flexible extended conformation, will not exhibit a propensity for developing an ordered secondary structure which could interact with the functional domains of fusion proteins, and will have minimal hydrophobic or charged character which could promote interaction with the functional protein domains. Typical surface amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, may also be used in the linker sequence. The length of the linker sequence may vary without significantly effecting the biological activity of the fusion protein. Exemplary linker sequences are described in U.S. Pat. Nos. 5,073,627 and 5,108,910, herein incorporated by reference.

Described above are affinity chromatography methods of purification. Not to be overlooked as alternative or combined methodologies are those employing conventional growth and biochemical purification.

For example, supernatants from systems which secrete recombinant protein into culture media may be first concentrated using a commercially available protein concentration filter, such as an Amicon or Millipore Pellicon ultrafiltration unit. Following the concentration step, the concentrate may be applied to a suitable purification matrix. For example, a suitable affinity matrix may comprise a counter structure protein (i.e., a protein to which a polypeptide binds in a specific interaction based on structure) or antibody molecule bound to a suitable support. Alternatively, or conjunctively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Gel filtration chromatography also provides a means of purifying polypeptides.

It is envisioned that changes to the proteins and polypeptides of the invention other than as already described will also work, e.g., substitutions, deletions, and insertions. These changes can be incorporated at the nucleic acid level or else may be administered in therapy and pharmaceutical composition applications as purified proteins.

Preliminarily, it is to be expected that conservative additions may be made that preserve function. A "conservative substitution" in the context of the subject invention is one in which an amino acid is substituted for another amino acid that has similar properties, such that one skilled in the art of peptide chemistry would expect the secondary structure and hydropathic nature of the polypeptide to be substantially unchanged for these regions. Other such conservative substitutions, e.g., include substitutions of entire regions having similar hydrophobicity characteristics, are well known. Mutagenic techniques for such replacement, insertion or deletion are well known to those skilled in the art (see, e.g., U.S. Pat. No. 4,518,584).

In certain embodiments, polypeptides of the invention may be prepared synthetically. Synthetic formation of the polypeptide or protein requires chemically synthesizing the desired chain of amino acids by methods well known in the art. Chemical synthesis of a peptide is conventional in the art and can be accomplished, for example, by the Merrifield solid phase synthesis technique [Merrifield, J., Am. Chem. Soc., 85:2149–2154 (1963); Kent et al., Synthetic Peptides in Biology and Medicine, 29 f f eds. Alitalo et al., (Elsevier Science Publishers 1985), and Haug, J. D., "Peptide Synthesis and Protecting Group Strategy", American Biotechnology Laboratory, 5 (1):40–47 (January/February. 1987)] all of which are herein incorporated by reference. Techniques of chemical peptide synthesis include using automatic peptide synthesizers employing commercially available protected amino acids, for example, Biosearch [San Rafael, Calif. (U.S.A.)] Models 9500 and 9600; Applied Biosystems, Inc. [Foster City, Calif. (U.S.A.)] Model 430; Milligen [a division of Millipore Corp.; Bedford, Mass. (U.S.A.)] Model 9050; and Du Pont's RAMP (Rapid Automated MultiplePeptide Synthesis) [Du Pont Compass, Wilmington, Del. (U.S.A.)]. Generally, however, such synthesis is expensive, and with limitations in the length of the peptides which can be produced (−50–100 amino acid residues), and therefore is not preferred. Allowance is made, however, for advances in the field that might facilitate or promote this means of synthesis in use of the invention.

EXAMPLE 15

Derivatization of Preferred Chemical Compositions

Whether synthesis is performed chemically or by making use of recombinant techniques, it may be desirable to further modify the polypeptide backbone prior to use as a diagnostic or therapeutic agent.

Covalent modifications of the protein or peptide are included within the scope of this invention. Such modifications may be introduced into the molecule by reacting targeted amino acid residues of the peptide with an organic derivatizing agent that is capable of reacting with selected side chains or terminal residues.

For example, cysteinyl residues react with α-haloacetates (and corresponding amines), such as chloroacetic acid or chloroacetimide, to give carboxymethyl or carboxyamidomethyl derivatives. Cysteinyl residues also are derivatized by reaction with bromotrifluoroacetone, α-bromo-β(5-imidozoyl)propionic acid, chloroacetyl phosphate, N-alkylmaleimides, 3-nitro-2-pyridyl disulfide, methyl 2-pyridyl disulfide, ρ-chloromercuribenzoate, 2-chloromercuri-4-nitrophenol, or chloro-7-nitrobenzo-2-oxa-1,3diazole.

Another amino acid, histidine, is easily derivatized by reaction with diethylprocarbonate at pH 5.5–7.0 because this agent is relatively specific for the histidyl side chain. ρ-Bromophenacyl bromide is also useful with the reaction preferably performed in 0.1M sodium cacodylate at pH 6.0.

Lysine and amino terminal residues may be reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride, trinitrobenzenesulfonic acid; O-methylisourea; 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high PK of the guanidine functional group. Furthermore, these reagents may react with the groups of lysine as well as the arginine epsilon-amino group.

Tyrosyl residues are well-known targets of modification for introduction of spectral labels by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'-N-C-N-R') such as 1-cyclohexyl-3-(2-morpholinyl(4-ethyl) carbodiimide or 1 -ethyl-3-(4-azonia-4,4-dimethylpentyl) carbodiimide.

Aspartyl and glutamyl residues are converted to asparaginyl and glutaminyl residues by reaction with ammonium ions. Glutaminyl and asparaginyl residues are frequently deamidated to the corresponding glutamyl and aspartyl residues. Alternatively, these residues are deamidated under mildly acidic conditions.

Other modifications include hydroxylation of proline and lysine, phosphorylation of hydroxyl groups of seryl or threonyl residues, methylation of the α-amino groups of lysine, arginine, and histidine side chains (Creighton, T. E., PROTEINS: STRUCTURE AND MOLECULAR PROPERTIES, W. H. Freeman & Co., San Francisco, pp. 79–86 (1983)) and herein incorporated by reference, acetylation of the N-terminal amine, and amidation of the C-terminal carboxyl groups.

Such derivatized moieties may improve the solubility, absorption, biological half life, and the like of compositions containing the therapeutic of the present invention. The moieties may alternatively eliminate or attenuate any undesirable side effect of the protein.

The screening method of the present invention provides means by which β-synuclein and derivatives thereof can be utilized for the detection of amyloidogenesis both in in vitro and in vivo test systems. Additionally, bigenic animals comprising at least a portion of the gene overexpressing α-synuclein, β-synuclein or heterozygous crosses thereof will have utility in screening for new anti-amyloidogenic agents. Incorporating β-synuclein, and peptides derived therefrom, into pharmaceutically acceptable compositions and treatment strategies provides methods for the treatment of neurodegenerative diseases such as Alzheimer's and Parkinson's.

Other embodiments of the present invention may occur to those of ordinary skill in the art in view of these teachings. Therefore, this invention is to be limited only by the following claims which include all other such embodiments and modifications when viewed in conjunction with the above specification and accompanying drawings.

---

We claim:

1. A transgenic mouse whose genome comprises a first and second transgenic nucleotide sequence, wherein the first transgenic nucleotide sequence comprises a human α-synuclein coding sequence or a human non-Aβ (NAC) region; and, the second transgenic nucleotide sequence comprises a human amyloid precursor protein (APP) coding sequence, each operably linked to a neuronal specific promoter and the human APP coding sequence comprises a Swedish or a Indiana mutation, wherein expression of said first and second transgenic nucleotide sequence results in amyloid deposits in the brain of said mouse.

2. An isolated neuronal cell from a transgenic mouse set forth in claim 1, wherein cells of the cell line overexpress a human α-synuclein coding sequence or a human non-Aβ (NAC) region.

3. A method of screening for agents that inhibit amyloidogenesis or α-synuclein aggregation, comprising:
   (a) providing a candidate agent, wherein optionally the candidate agent is a candidate therapeutic agent;
   (b) providing a transgenic mouse as set forth in claim 1, or a cell line as set forth in claim 2;
   (c) administering the candidate agent to the cell line or transgenic mouse; and
   (d) evaluating the effect of said candidate agent on amyloidogenesis or amyloid deposition.

4. The method of claim 3, wherein the effect of the candidate agent on amyloidogenesis or amyloid deposition comprises inhibition of α-synuclein aggregation in neurons.

5. The transgenic mouse of claim 1, wherein an SV40-derived intron operably links the promoter with the first or second transgenic nucleotide sequence.

6. The transgenic mouse of claim 1, wherein the first or second transgenic nucleotide sequence comprises an intron.

7. The transgenic mouse of claim 1, wherein the intron comprises an SV40-derived intron.

* * * * *